United States Patent
Graumann et al.

(10) Patent No.: US 8,886,286 B2
(45) Date of Patent: Nov. 11, 2014

(54) DETERMINING AND VERIFYING THE COORDINATE TRANSFORMATION BETWEEN AN X-RAY SYSTEM AND A SURGERY NAVIGATION SYSTEM

(75) Inventors: Rainer Graumann, Hoechstadt (DE); Gerhard Kleinszig, Forchheim (DE); Martin Ringholz, Erlangen (DE)

(73) Assignee: Siemens Aktiengesellschaft, Munich (DE)

(*) Notice: Subject to any disclaimer, the term of this patent is extended or adjusted under 35 U.S.C. 154(b) by 0 days.

(21) Appl. No.: 13/698,772

(22) PCT Filed: Apr. 20, 2011

(86) PCT No.: PCT/EP2011/056372
§ 371 (c)(1),
(2), (4) Date: Nov. 19, 2012

(87) PCT Pub. No.: WO2011/144412
PCT Pub. Date: Nov. 24, 2011

(65) Prior Publication Data
US 2013/0066196 A1    Mar. 14, 2013

(30) Foreign Application Priority Data

May 18, 2010 (DE) .......................... 10 2010 020 781

(51) Int. Cl.
| | |
|---|---|
| *A61B 5/05* | (2006.01) |
| *A61B 6/00* | (2006.01) |
| *A61B 6/12* | (2006.01) |
| *G01B 15/00* | (2006.01) |
| *G01B 21/04* | (2006.01) |
| *A61B 17/00* | (2006.01) |
| *A61B 19/00* | (2006.01) |

(52) U.S. Cl.
CPC . *A61B 6/12* (2013.01); *A61B 6/547* (2013.01); *A61B 2017/00725* (2013.01); *A61B 2019/4894* (2013.01); *A61B 6/582* (2013.01); *A61B 19/5244* (2013.01); *A61B 6/4441* (2013.01); *A61B 2019/527* (2013.01); *G01B 15/00* (2013.01); *A61B 19/54* (2013.01); *G01B 21/042* (2013.01); *A61B 2019/5295* (2013.01); *A61B 2019/5255* (2013.01); *A61B 2019/5495* (2013.01)
USPC ............ 600/414; 600/407; 600/424; 606/130

(58) Field of Classification Search
USPC ................... 600/407–430; 606/130
See application file for complete search history.

(56) References Cited

U.S. PATENT DOCUMENTS

| | | | | |
|---|---|---|---|---|
| 6,533,455 | B2* | 3/2003 | Graumann et al. ........... | 378/205 |
| 6,851,855 | B2 | 2/2005 | Mitschke et al. | |
| 7,519,415 | B2* | 4/2009 | Mitschke et al. ............. | 600/424 |

(Continued)

FOREIGN PATENT DOCUMENTS

| | | |
|---|---|---|
| DE | 102 02 091 A1 | 8/2003 |
| DE | 102 15 808 A1 | 11/2003 |

(Continued)

*Primary Examiner* — Sanjay Cattungal
(74) *Attorney, Agent, or Firm* — Laurence A. Greenberg; Werner H. Stemer; Ralph E. Locher

(57) ABSTRACT

The device enables the detection of positions of the navigation marking elements on a reference star by way of at least two projection images taken by an X-ray system at different pivoting angles of a C-arm. The positions of the navigation marking elements on the reference star are also calculated by a navigation system tracking camera. The transformation from the coordinate system of the navigation system into the coordinate system of the X-ray system is calculated from the position of the reference star detected by the X-ray system and the position of the reference star detected by the tracking camera. The navigation marking elements are located outside of the volume which is reconstructed by way of the imaging process in order to prepare tomographic images. The positions of the navigation marking elements are determined from two-dimensional projections. All the navigation marking elements need only be detected by at least two projection images.

15 Claims, 4 Drawing Sheets

(56) References Cited

U.S. PATENT DOCUMENTS

| | | |
|---|---|---|
| 7,643,867 B2 | 1/2010 | Solar et al. |
| 7,672,709 B2 | 3/2010 | Lavallee et al. |
| 7,778,690 B2 | 8/2010 | Boese et al. |
| 2002/0044631 A1* | 4/2002 | Graumann et al. ............ 378/205 |
| 2003/0179856 A1* | 9/2003 | Mitschke et al. ............. 378/205 |
| 2005/0054915 A1* | 3/2005 | Sukovic et al. ............... 600/424 |
| 2005/0163279 A1* | 7/2005 | Mitschke et al. ............... 378/62 |
| 2011/0015519 A1 | 1/2011 | Graumann |

FOREIGN PATENT DOCUMENTS

| | | |
|---|---|---|
| DE | 10 2006 024 425 A1 | 11/2007 |
| DE | 10 2009 034 671 A1 | 1/2011 |
| FR | 2 841 118 A1 | 12/2003 |
| WO | 2004/075768 A2 | 9/2004 |
| WO | 2009/109552 A1 | 9/2009 |

* cited by examiner

DETERMINING AND VERIFYING THE COORDINATE TRANSFORMATION BETWEEN AN X-RAY SYSTEM AND A SURGERY NAVIGATION SYSTEM

BACKGROUND OF THE INVENTION

Field of the Invention

The invention relates to the improved determination and verification of a coordinate transformation between an X-ray system and a surgical operation navigation system and a method and an apparatus therefor.

A surgical operation navigation system usually has a stereoscopic tracking camera. So-called navigation stars having at least three marking elements, for example balls, are attached to a body part of a patient. The marking elements are made of a material, or provided with a coating, which reflects infrared radiation. Surgical instruments can also be provided with a navigation star with said three marking elements. Since the spatial relationship between the navigation star and the tip of the surgical tool used to perform the actual operation on the body is known, the surgical operation navigation system is able to determine the position of the surgical instrument or its tip in the human body. To this end, the surgical operation navigation system emits infrared radiation, for example, and the radiation reflected by the marking elements of the navigation star is detected by means of the stereoscopic camera. The data detected by the stereoscopic camera can be used for the continuous determination of the position of the navigation star on the surgical instrument in space and hence for the determination of the position of the tip of the surgical instrument in the body.

The surgeon wishes to obtain image data on the interior of the site of the operation. To this end, X-ray systems with a so-called C-arm are used, for example. To determine information on the interior of the site of the operation, the C-arm is pivoted into different positions and, after the pivoting, a projection image in this position is created by X-raying. The image data obtained thereby represents the attenuation of an X-ray beam on passing through tissue with the respective projection. The imaging process can be used to reconstruct tomographic images which provide the surgeon with three-dimensional image data on individual slices of the interior of the patient or the site of the operation.

To ensure that the surgical operation navigation system is particularly helpful to the surgeon, the position of the surgical instrument or its tip in the body should to be displayed in previously obtained image data. Therefore, surgical navigation is a combination of image data of an object's volume and the localization of surgical instruments. Conventional surgical navigation substantially uses three methods for this.

With the first method, preoperative 3D image sets taken with a computed tomography scanner or a magnetic resonance imaging scanner are used for example. To achieve conformity between the preoperative data set and the position of the patient in the operating theatre, it is necessary to detect anatomical markings or previously implanted reference points on the patient and then adapt the coordinates between the surgical instruments and the image data set. This method has the drawback that the image data are not recorded in the position during the operation and any anatomical changes that may occur in the region of the operation during the surgical intervention may not be taken into account.

The second method uses a marker ring with a calibration template, said marker ring being attached to the image intensifier on a mobile C-arm of an X-ray system in 2D mode. Manual comparison between the anatomy and the image data is not necessary, but the representation is exclusively a two-dimensional projection image. This provides less information when compared with a representation of individual slices with a three-dimensional method and is therefore not preferred.

The third method uses a C-arm for intraoperative generation of a three-dimensional data set which can be used directly for navigation during the operation without any further recording steps being required. This recorded data is stored in the system by a previously performed system calibration and does not have to be regenerated during clinical application.

The X-ray system with the C-arm enables comparatively simply and quickly updated image data on the interior of the site of the operation to be obtained during the operation. The X-ray system with the C-arm is comparatively compact and can be moved during the operation in the operating theatre so that the site of the operation can be X-rayed once again. To enable a surgical instrument or its tip to be displayed in the tomographic images, it is necessary to determine the coordinate transformation between the detected image data and the surgical operation navigation system.

During the determination of this coordinate transformation, a marking ring is arranged on the image intensifier of the C-arm of the X-ray system. A reference star is arranged on the patient. The navigation system camera system is set up in order to detect both the marking ring and the reference star on the patient. The X-ray system is moved in its working position to take X-rays of the patient. The coordinates of the marking ring are detected by the surgical operation navigation system. The C-arm is pivoted stepwise and an X-ray is taken after each pivoting process. Three-dimensional image data is generated from the X-ray measurements. The image data and the coordinates are transferred to the surgical operation navigation system. The mobile X-ray system can now be removed from the site of the operation. The surgeon can now start the operation when the accuracy of the coordinate transformation has been verified.

The accuracy of the coordinate transformation can be verified by a pointer instrument tracked by the surgical operation navigation system, which can make contact with defined structures for example the anatomy, the reference star etc., wherein it has to make contact with at least three points. The position of the pointer instrument is displayed in the previously determined tomographic images. The surgeon verifies visually that the pointer instrument is depicted in such a way that it makes contact with the corresponding structure in the image data set with sufficient accuracy. If this visual check identifies only a small deviation, the coordinate transformation is considered to be sufficiently accurate for the navigation-guided intervention. The accuracy achieved is about +/−2 mm.

BRIEF SUMMARY OF THE INVENTION

It is an object of the invention to provide an improved method and an improved apparatus for the determination of the coordinate transformation between the image data and the surgical operation navigation system. It is a further object of the invention to provide a method and an apparatus for the verification of a coordinate transformation between the image data and the surgical operation navigation system. Furthermore, the accuracy of the navigation system used intraoperatively or during the previous medicinal procedure or the determination of its position and recording is to be verified. A further object consists in the provision of automatic quality control (in particular for the image recording) for the navigation system.

This object is achieved by the attached claims, in particular by a method for the determination of a coordinate transformation for verifying a recording and by a coordinate transformation apparatus and by a surgical operation system and a computer program product.

One aspect of the invention is to check the previous recording (i.e. coordinate transformation) of the navigation system by performing a reference recording which is then compared with the previous recording. According to an advantageous embodiment, a threshold value for a maximum permissible deviation can be predetermined. If the threshold value is exceeded, an alarm signal is emitted and/or the previous recording can be automatically or semi-automatically updated (following a confirmation signal from a user).

The reference recording can be made using a 3D C-arm scan or using a plurality of 2D C-arm images.

One aspect of the invention relates to a method for determining a reference object coordinate transformation between a surgical operation navigation system and an X-ray system having a pivotable C-arm for detecting the interior of an object. The marking elements of a reference object are arranged in a region which is detected by the surgical operation navigation system and the X-ray system in at least two pivoting positions of the C-arm. The position of the marking elements of the reference object is detected with the surgical operation navigation system. The marking elements of the reference object are detected with the X-ray system from at least two projections. The position of the reference object is determined from at least two two-dimensional projection images. The reference object coordinate transformation is determined from the position of the marking elements of the reference object detected by the surgical operation navigation system and from the position of the marking elements of the reference object determined by the X-ray system. According to one embodiment of the invention, the term "reference object coordinate transformation" can also be understood to mean a reference coordinate transformation for the same object.

The reference object can be a reference star having at least three, preferably four, marking elements which is tracked by a camera of a surgical operation navigation system.

The invention provides an exact calibration and/or recording method and verification method for a recording that has already been made without reducing the reconstructed volume which can be evaluated by the imaging process and is available for both for the treatment and the navigation.

Hence the invention can also be used to verify the accuracy of the navigation system used to date or its recording. This is performed with a reference recording or with a reference coordinate transformation, as mentioned above. The verification is performed automatically by comparing the previous recording/coordinate transformation with the reference recording/coordinate transformation. Hence the comparison relates to the automatic recording of the navigation system and the calculated coordinate transformation. In an advantageous embodiment, the result of the comparison can be provided as a quality criterion or quality standard. In an advantageous embodiment, the result can also be used to adapt or improve the recording of the navigation system.

The expression "coordinate system of the X-ray system" should be interpreted as meaning that it includes the coordinate systems of the individual tomographic images since the tomographic images are determined from projections obtained with the X-ray system. The surgical operation navigation system can have a stereoscopic camera. However, it is also conceivable for the position of reference markings to be determined by the surgical operation navigation system by means of inductive methods. The surgical operation navigation system determines the position of the reference star in the coordinate system of the surgical operation navigation system.

The reference object can be attached to a patient, for example to a bone of the patient. However, the reference object can also only be fixed to the patient's skin.

The method also includes the step of the detection of data representing the interior of an object by means of X-radiation during the detection of the position of the marking elements of the reference object with the X-ray system from at least two projections. Tomographic images representing the interior of the object are generated from the data. Obviously, more than two projections are necessary to generate the three-dimensional data set for the tomographic images. These data can be sent to the surgical operation navigation system. Navigation information can be displayed in the tomographic images, for example the position of a surgical instrument or the position of the tip of a surgical instrument.

Consequently, the surgeon knows the position at which the tip of the surgical instrument is located.

The invention also discloses a method for the determination and/or verification of a C-arm coordinate transformation between a surgical operation navigation system and an X-ray system with a C-arm. The surgical operation navigation system detects the position of a reference object arranged on the patient's body. The C-arm is pivoted into at least two positions. The position of the C-arm is determined with the surgical operation navigation system after each pivoting. Data representing the interior of the object is determined by means of X-radiation after each pivoting in this position. This data, which is determined in a plurality of projections, can be used to create tomographic images. The C-arm coordinate transformation between the surgical operation navigation system and the X-ray system is determined on the basis of the at least two detected positions of the C-arm. The C-arm coordinate transformation can be compared with the previously described reference object coordinate transformation.

The expression "C-arm coordinate transformation" also includes a coordinate transformation into the coordinate system of the individual tomographic images producing three-dimensional image data, since these were determined from the projection images detected by the X-ray system with the C-arm. The coordinate transformation between the X-ray system or the tomographic images and the surgical operation navigation system is determined by means of two different methods. This redundancy enables the quality of the respective coordinate transformation to be determined and, if the deviation is too high, a warning can be issued. In this case, the operator can perform a manual re-adjustment. It is also possible to change evaluation parameters and/or determine one of the coordinate transformations for use. These further steps can be triggered and/or performed automatically without user interaction.

The method also includes the step of the generation of tomographic images from data representing the interior of the object. Image data having a plurality of tomographic images can be sent to the surgical operation navigation system. Navigation information can be displayed in the tomographic images.

The method can be implemented by the surgical operation navigation system. To this end, the surgical operation navigation system can give instructions to the X-ray system. However, it is also conceivable for the method to be implemented in a separate control unit which issues instructions to both the surgical operation navigation system and the X-ray system. The control device or the surgical operation navigation system can be a programmable computer with a CPU and a memory which carry out the method. The invention also discloses a computer program product with program code means which carry out the steps of the above-mentioned method when they are loaded in a computer and executed by the computer.

The object of the invention is also achieved by a coordinate transformation apparatus designed to determine a reference object coordinate system between a surgical operation navigation system and an X-ray system with a C-arm. The coordinate transformation apparatus can be implemented in the surgical operation navigation system or be a separate apparatus, for example the above-mentioned programmable computer. The coordinate transformation apparatus can also be made of discrete logic elements. The coordinate transformation apparatus has an X-ray system instruction mechanism which issues an instruction to an X-ray system. The X-ray system instruction mechanism can, for example, have an interface implemented by means of a plug-in connection, for example a network interface. The X-ray system instruction apparatus can also be an inter-program communication interface.

The coordinate transformation apparatus has a surgical operation navigation instruction mechanism which issues an instruction to a surgical operation navigation system. The surgical operation navigation system instruction mechanism can have an interface implemented by means of a plug-in connection or can be an inter-program communication interface. The coordinate transformation apparatus has a control device which is designed to instruct the surgical operation navigation system to detect the position of marking elements of a reference object by means of the surgical operation navigation system instruction mechanism. The reference object can be the above-described reference star with at least three marking elements.

The control device is designed to instruct the X-ray system by means of the X-ray system instruction mechanism to detect the marking elements of the reference object by taking X-rays from at least two projections. The control device is designed to instruct the X-ray system, by means of the X-ray system instruction mechanism, to determine the position of the marking elements from at least two two-dimensional projection images. The control device is also designed to determine the reference object coordinate transformation from the position of the reference object detected by the surgical operation navigation system and the position of the reference object detected by the X-ray system.

The control device can be designed to instruct the X-ray system, by means of the X-ray system instruction mechanism, to detect data representing the interior of the object, by means of X-radiation on the detection of the position of the reference object with the X-ray system from at least two projections. The control device can be designed to instruct the X-ray system, by means of the X-ray system instruction mechanism, to generate tomographic images from the data representing the interior of the object. The tomographic images can be sent to the surgical operation navigation system. The control device can instruct the surgical operation navigation system, by means of the surgical operation navigation system instruction mechanism, to display navigation information in the tomographic images. This enables the surgeon to carry out the navigation-guided operation.

All marking elements have to be contained in at least two, preferably in exactly two, projection images. Preferably, the two images should be virtually orthogonal to each other. In at least one projection image, the coordinate transformation apparatus will not detect all marking elements by taking X-rays with the X-ray system arranged on the C-arm because the X-ray beam detects the interior of the object and/or the volume to be reconstructed in an angle such that the X-ray beam does not pass through all marking elements. Although not all marking elements are detected by the X-ray beam, the volume to be reconstructed is completely detected.

The coordinate transformation apparatus can have a verification device. The control device can also be designed to instruct the surgical operation navigation system, by means of the surgical operation navigation system instruction mechanism, to detect the position of a reference object. The control device can be designed to instruct the X-ray system, by means of the X-ray system instruction mechanism, to pivot the C-arm into at least two positions, and to instruct the surgical operation navigation system, by means of the surgical operation navigation system instruction mechanism, to detect the position of the C-arm, for example by means of a tracking camera, after the pivoting. The control device can also be designed to instruct the X-ray system, by means of the X-ray system instruction mechanism, to detect data representing the interior of the object by means of X-radiation after the pivoting. The control device can be designed to determine a C-arm coordinate transformation from the positions of the C-arm detected by the surgical operation navigation system and the position of the reference object detected by the surgical operation navigation system.

The control device instructs the verification device to compare the C-arm coordinate transformation with the reference object coordinate transformation. This enables the accuracy of the coordinate transformations to be determined. If the values of the coordinate transformations deviate from each other by more than a predetermined threshold value, the user can be alerted to this by a warning and the user can react to the error. A re-adjustment, for example a virtual displacement of the data with respect to each other can be performed user-controlled or automatically. These inputs can be used to repeat the recording. There is no need to re-X-ray the patient. The new calculation and the result of the method according to the invention can be checked for plausibility. This can be performed in an optional additional method step following the other steps. To this end, the data is displayed by one or both coordinate transformations on a display device. It is also possible for the overshooting of permissible minimum values, maximum values and/or other parameters to be verified automatically. It is also possible to use a menu-driven control to make further corrections here (in particular to the recorded data) including when in operation (also manually).

The control device can be designed to instruct the X-ray system, by means of the X-ray system instruction mechanism, to generate tomographic images from data representing the interior of the object. The tomographic images can be sent to the surgical operation navigation system. The control device can be designed to instruct the surgical operation navigation system, by means of the surgical operation navigation system instruction mechanism, to display navigation information in the tomographic images.

The invention also relates to a surgical operation system having an X-ray system with a C-arm, a surgical operation navigation system and the above-described coordinate transformation apparatus.

The invention will now be explained with reference to the attached figures.

DESCRIPTION OF THE INVENTION

Figure 1:
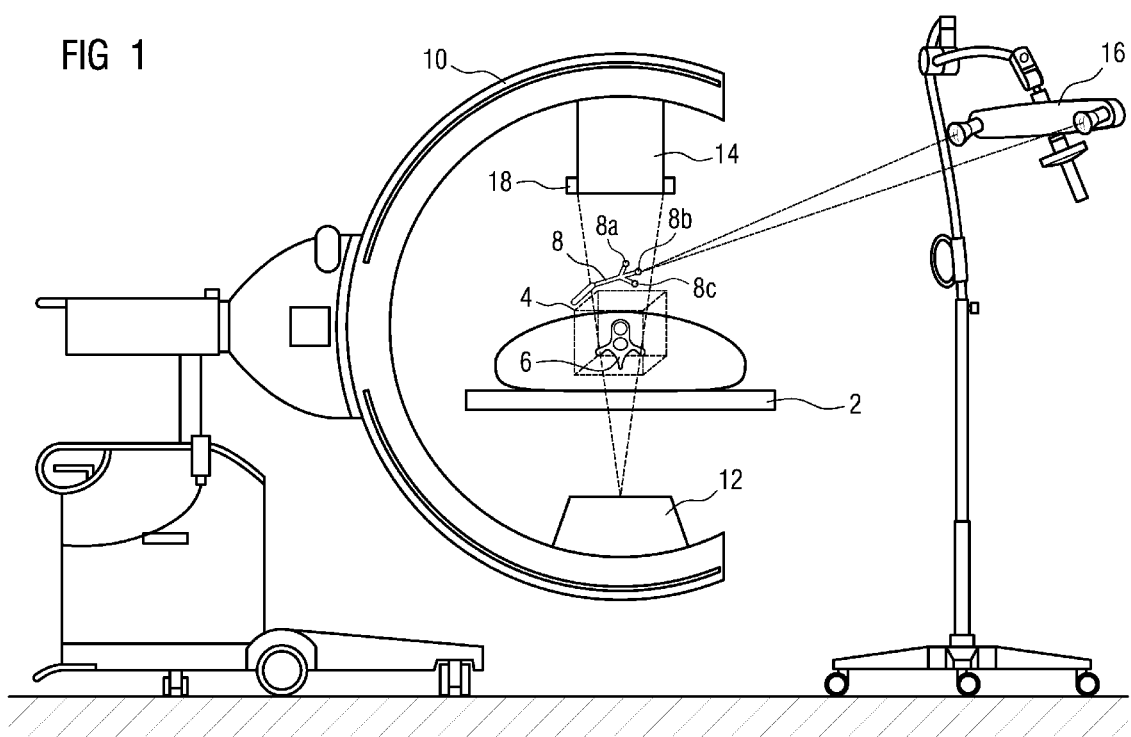
FIG. 1 shows a surgical environment in which a C-arm of an X-ray system is located in a first pivoting position.

FIG. 1 shows an operating table 2, which is preferably made of X-ray permeable carbon. On the operating table there is the volume of an object 4 of which projection images are produced by means of X-raying and then tomographic images of three-dimensional image data are generated. A reference star 8 is arranged on a spine 6. The reference star 8 has three marking elements 8a, 8b, 8c, which reflect light in the infrared range. A stereoscopic camera 16 emits infrared radiation and detects the marking elements 8a, 8b, 8c of the reference star 8 by means of two cameras. The data detected by the stereoscopic camera 16 is forwarded to a surgical operation navigation system.

The surgical environment includes an X-ray system with a C-arm 10 on which an X-ray source 12 and an X-ray detector or X-ray intensifier 14 are arranged. The C-arm can be pivoted in order to take X-rays of the volume of the object 4 from different pivoting angles or projections. Three-dimensional tomographic images are generated from the projection images created in different projection angles. A reference marking 18, which also reflects infrared radiation is attached to the X-ray detector or X-ray intensifier 14. The reference marking 18 can be detected by the stereoscopic camera 16 of the surgical operation navigation system.

The X-ray system with the C-arm 10 is displaceable so that it can be pushed toward the operating table 2 before and/or during an operation in order to X-ray an object 4 corresponding to the site of the operation. When the X-rays have been taken, the X-ray system with the C-arm 10 can be pushed away again to give the surgeon free access to the site of the operation.

Figure 2:
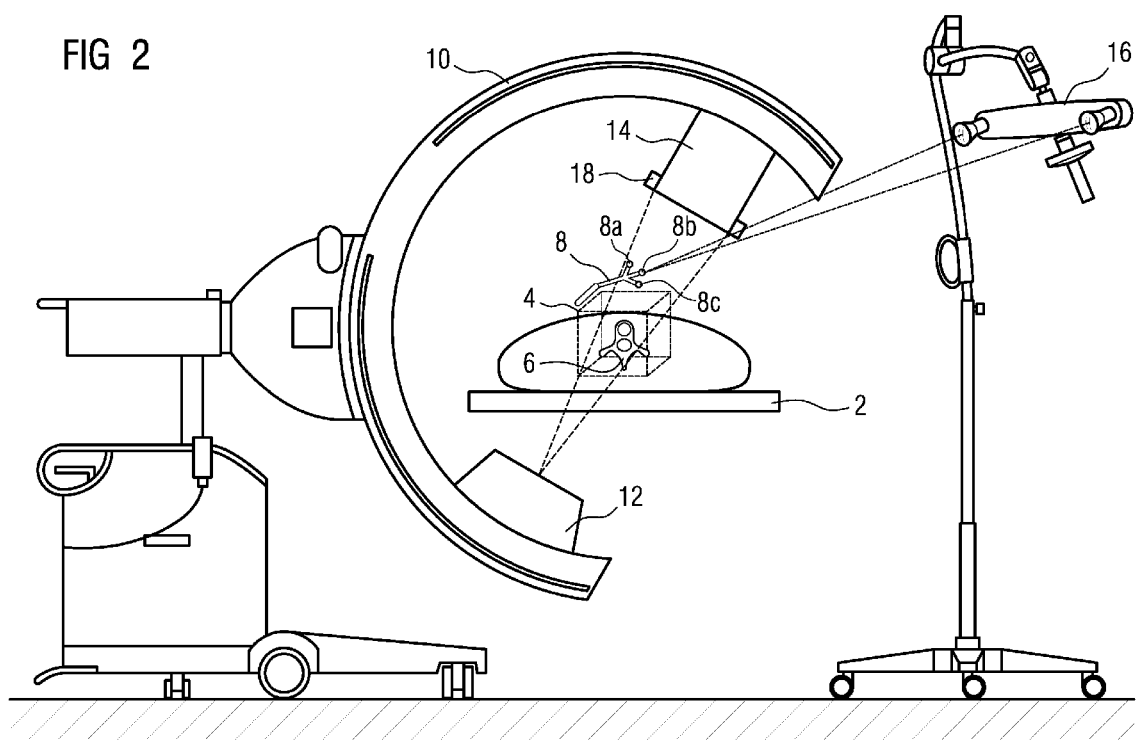
FIG. 2 shows a surgical environment in which the C-arm of the X-ray system is located in a second pivoting position.

FIG. 2 substantially corresponds to FIG. 1, wherein the C-arm 10 has adopted another pivoting position and the object 4 is analyzed with X-radiation from another projection.

Figure 3:
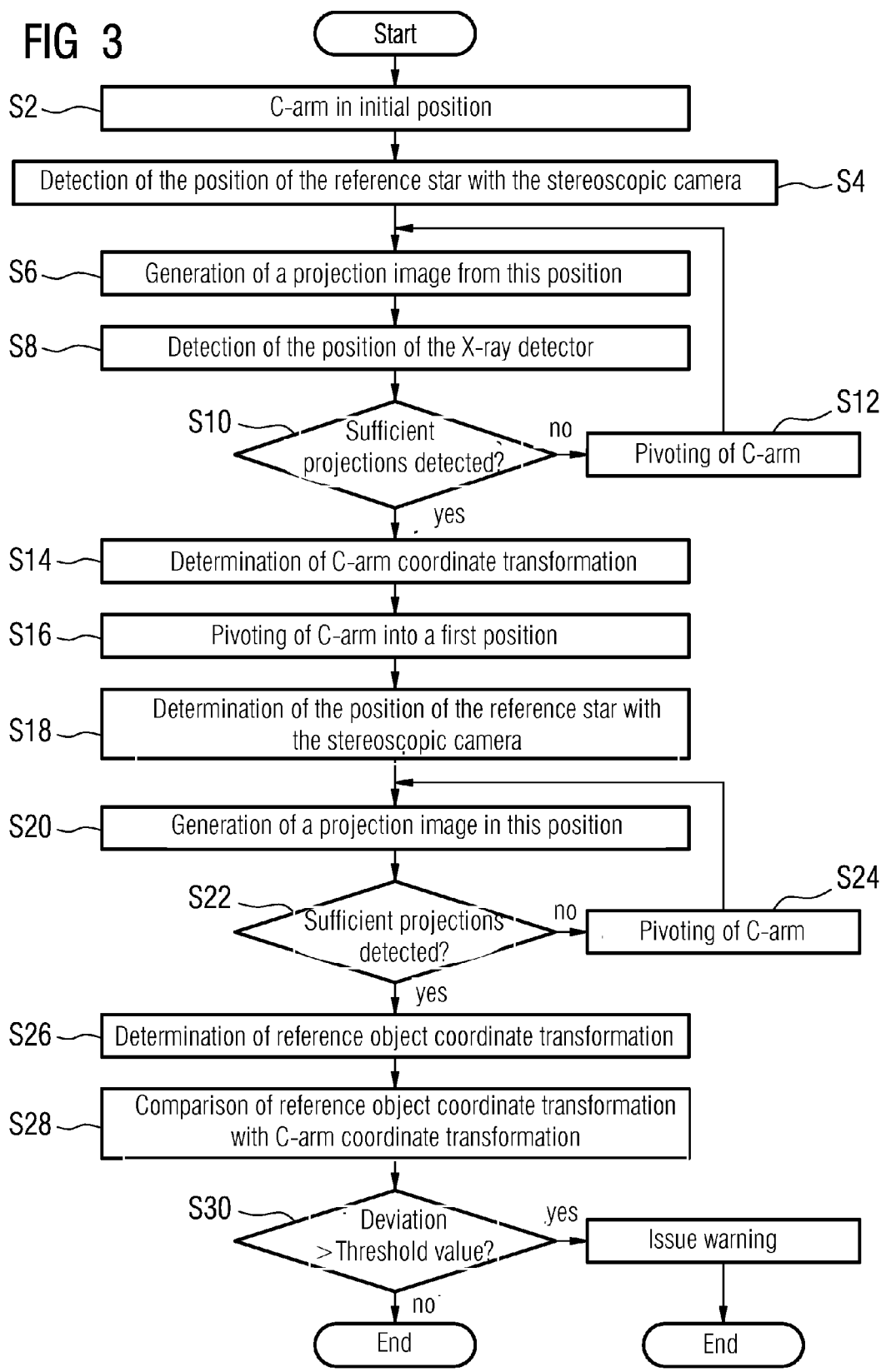
FIG. 3 is a flow diagram of the method according to the invention.

The invention will now be explained with reference to FIGS. 1 to 3. During the determination of the C-arm coordinate transformation, the C-arm is for example brought into initial position shown in FIG. 1 S2. The stereoscopic camera 16 detects the position of the reference star 8 by means of infrared light reflected by the marking elements 8a, 8b, 8c emitted by the surgical operation navigation system S4. In the context of this invention, the expression "position" also includes the orientation. In this position of the C-arm, the X-ray system creates a projection image of the object 4 S6. The position of the X-ray detector or X-ray intensifier 14 is also detected with the aid of the reference marking 18 by the stereoscopic camera 16 S8. The C-arm 10 is pivoted stepwise S12, as shown in FIG. 2, and after each pivoting, a further projection image is generated S6 and the position of the reference marking 18 is detected by the surgical operation navigation system S8 until sufficient projections have been detected S10. The positions of the X-ray detector or X-ray intensifier 14 detected by the stereoscopic camera 16 and the position of the reference star 8 detected by the stereoscopic camera 16 are used to determine the C-arm coordinate transformation between the coordinate system of the surgical operation navigation system and the coordinate system of the X-ray system S14. As mentioned above, the expression "coordinate system of the X-ray system" also includes the coordinate system of the images, since the images are generated from the projection images created by the X-ray system.

The quality of the C-arm coordinate transformation is now checked by means of a reference object coordinate transformation or a reference coordinate transformation of the object. To this end, the C-arm 10 is pivoted into a first position as shown, for example, in FIG. 1 S16. The stereoscopic camera 16 of the surgical operation navigation system determines the position of the marking elements 8a, 8b, 8c of the reference star 8 S18. The system uses the X-ray source 12 and the X-radiation detector or X-radiation intensifier 14 to take a projection image S20. The X-ray beams also pass through the marking elements 8a, 8b, 8c of the reference star 8. The C-arm 10 is pivoted S24 and a further projection image is created S20 with which the X-radiation passes through the marking elements 8a, 8b, 8c of the reference star. When at least two projection images have been created S22, the positions of the marking elements 8a, 8b, 8c of the reference star in the coordinate system of the X-ray system can be determined from two-dimensional projection images and hence in the coordinate system of the tomographic images. The reference object coordinate transformation between the navigation system coordinate system and X-ray system coordinate system can now be determined from the position of the marking elements 8a, 8b, 8c of the navigation star 8 in the surgical operation navigation coordinate system determined by the surgical operation navigation system and the position of the marking elements 8a, 8b, 8c, 8b of the reference star 8 determined by the X-ray system in the X-ray system coordinate system S26.

The marking elements do not have to be detected in all projections and pivoting positions of the C-arm since the volume of the object 4 which can be detected by means of the X-ray system with the C-arm 10 is relatively small. The edge length of the volume 4 which can be detected with the C-arm 10 on which the X-ray source 12 and the X-ray detector 14 are arranged is typically the half the dimension of the X-ray detector or X-ray intensifier 14. If the length of the X-ray detector 14 is 24 cm in one direction, the X-ray system is able to detect a cube with an edge length of 12 cm. From this volume 4, imaging methods are able to generate a three-dimensional reconstruction as a data set and tomographic images. The marking elements 8a, 8b, 8c of the reference star 8 are located outside of the region from which the imaging process makes a three-dimensional reconstruction of an image data set for tomographic images. Therefore, the position of the marking elements 8a, 8b, 8c of the reference star 8 is determined from two-dimensional projections. Therefore, the marking elements 8a, 8b, 8c of the reference star 8 only have to be identifiable in a few projection images and not in all projection images. The expression "marking elements" should be interpreted as meaning that it includes all marking elements required for the navigation arranged on the reference star. All the marking elements 8a, 8b, 8c of the reference star 8 only have to be detected in a few projection images.

All marking elements have to be contained in at least two, preferably in exactly two, projection images. Preferably, the two images should be virtually orthogonal to each other. In at least one projection image, not all marking elements are detected by taking X-rays because the X-ray beam detects the interior of the object and/or the volume to be reconstructed in a such an angle that the X-ray beam from the X-ray source 12 to the X-ray detector or X-ray intensifier 14 does not pass through all marking elements. Although not all marking elements are detected by the X-ray beam, the volume to be reconstructed is completely detected.

The reference object coordinate transformation can be depicted mathematically as follows:

$$\vec{X}_{camera} = A \cdot \vec{X}_{c\text{-}arm} + \vec{b};$$

wherein A is the rotation matrix with the size 3×3 and b is a displacement vector with three dimensions.

Therefore, the rotation matrix A and the displacement vector b contain 12 unknowns which can be determined by the three-dimensional positions of the three marking elements of the reference star.

When the reference object coordinate transformation has been determined by this procedure, it can be compared with the C-arm coordinate transformation S28. If the deviation between the two coordinate transformations is higher than a predetermined threshold value, a warning can be issued. In this case, the operator can perform a manual re-adjustment, change evaluation parameters, choose one of the coordinate transformations etc.

The X-ray system can use the method mentioned in the introduction to determine tomographic images from the detected projection images. The tomographic images can be sent as an image data set to the surgical operation navigation system so that the image data can be displayed there together with the position of the surgical instrument during the operation.

As soon as the coordinate transformation has been determined with sufficient accuracy, the surgeon can start the navigation-guided operation. The screen of the surgical operation navigation system displays the tomographic image data determined by the X-ray system and the position of a surgical instrument, in particular its tip. Hence, the surgeon knows during the operation where the tip of the surgical instrument is located on the object 4.

This embodiment was described such that first the C-arm coordinate transformation is determined and the C-arm coordinate transformation is verified by the reference object coordinate transformation. However, the invention is not restricted to this embodiment. The reference object coordinate transformation can be determined first and then verified with the subsequently determined C-arm coordinate transformation. It is also possible to determine only the reference object coordinate transformation and then start the navigation-guided operation.

The embodiment was described such that the C-arm coordinate transformation is determined first and then the reference object coordinate transformation. It should be understood that the C-arm can only be successively pivoted once and hereby projection images created, wherein both the interior of the object 4 to be analyzed, from which the three-dimensional image data is to be created, and the marking elements 8a, 8b, 8c of the reference star 8 are detected by at least a few projection images, wherein the marking elements 8a, 8b, 8c are located outside of the region from which three-dimensional image data is to be created. This means that step S6 and step S20 are performed simultaneously in that it is ensured that the projection image includes both the interior of the object 4 and the marking elements 8a, 8b, 8c of the reference star 8. The result is that the method steps named in the claims can be performed in any sequence.

Figure 4:
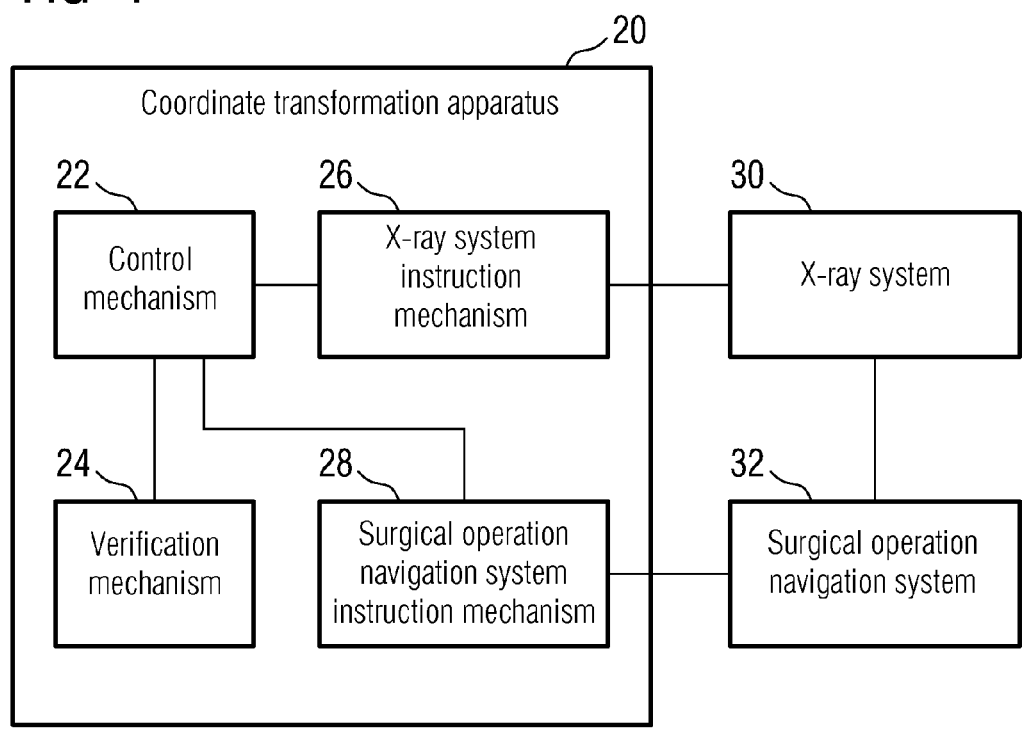
FIG. 4 is a schematic diagram of the interaction of a coordinate transformation apparatus with the X-ray system and a surgical operation navigation system.

FIG. 4 shows the schematic structure of the coordinate transformation apparatus 20 and the interfaces to the X-ray system 30 and the surgical operation navigation system 32.

The coordinate transformation apparatus 20 has a control apparatus 22, a verification device 24, an X-ray system instruction mechanism 26 and a surgical operation navigation system instruction mechanism 28. The control device 22 issues instructions to the X-ray system 30 via the X-ray system instruction mechanism 26. The control device 22 also issues instructions to the surgical operation navigation system 32 via the surgical operation navigation system instruction mechanism 28. The X-ray system instruction mechanism 26 and the surgical operation navigation system instruction mechanism 28 can be implemented by interfaces with a plug-in connection. However, it is also possible to embody the X-ray system instruction mechanism 26 and the surgical operation navigation system instruction mechanism 28 by interprogram communication interfaces.

The control device 22 instructs the surgical operation navigation system 32 via the surgical operation navigation system instruction mechanism 28 to detect the position of the marking elements 8a, 8b, 8c of the reference star 8. The control device 22 instructs the X-ray system 30 via the X-ray system instruction apparatus 26 to create a projection image which also includes the marking elements 8a, 8b, 8c of the reference star 8. The control device 22 instructs the X-ray system 30 via the X-ray system instruction mechanism 26 to pivot the C-arm 10 into another position. The control device 22 instructs the X-ray system 30 to create a further projection image which is detected by the marking elements 8a, 8b, 8c, 8d of the reference star 8.

The control device 22 instructs the X-ray system 33 via the X-ray system instruction mechanism 26 to calculate the position of the marking elements 8a, 8b, 8c of the reference star 8 from two-dimensional projections and output them in the coordinate system of the X-ray system to the control device 22. The control device 22 then instructs the surgical operation navigation system 32 via the surgical operation navigation system instruction mechanism 28 to output the position of the marking elements 8a, 8b, 8c of the reference star 8 in the coordinate system of the surgical operation navigation system to the control device 22. The control device can therefore determine the reference object coordinate transformation. The control device 22 sends the reference object coordinate transformation to the verification device 24. The control device 22 also sends the C-arm coordinate transformation, which was determined as described earlier with reference to FIG. 3, to the verification mechanism 24. The verification device 24 compares the reference object coordinate transformation with the C-arm coordinate transformation. If the deviation is equal to or lower than a predetermined threshold value, the determination of the coordinate transformation between the surgical operation navigation system and the X-ray system and hence the tomographic images of the three-dimensional image data set are sufficiently accurate. Therefore, the surgeon can start the operation. If the deviation is greater than a predetermined threshold value, a warning can be output resulting in the above-described intervention by the operator.

The invention discloses that by means of at least two projection images, the X-ray system detects the position of the navigation marking elements on the reference star at different pivoting angles of the C-arm. The position of the navigation marking elements on the reference star is also calculated by the tracking camera of the navigation system. The transformation of the coordinate system of the navigation system into the coordinate system of the X-ray system is calculated from the position of the reference star detected by the X-ray system and the position of the reference star detected by the navigation camera. The navigation marking elements are located outside of the volume which is reconstructed by means of imaging processes in order to prepare tomographic images. The position of the navigation marking elements is determined from two-dimensional projections. All the navigation marking elements need only be detected by at least two projection images.

The method according to the invention has the advantage that that it is able to verify the accuracy of a previously determined coordinate transformation. The method according to the invention also has the advantage that only one reference star is required. This enables preoperative image data sets to be sent to the surgical operation navigation system in a quick and simple way. The invention also has the advantage that, during an operation, the interior of the object changed by the operation can be determined and three-dimensional image data sets of the changed object can be created comparatively quickly and with comparatively simple means in order to be used for a navigation-guided operation.

The invention is not restricted to medical operations. The invention can also be used in the examination of other objects, for example the examination of an industrial, physical or archeological item.

Finally, reference is made to the fact that the invention can also be embodied as a distributed system so that individual modules of the coordinate transformation apparatus 20 can also be distributed or provided on different entities, for example in the navigation system 16, 32 and/or in the X-ray system 12, 14 or in separate entities in a data exchange network.

LIST OF REFERENCE CHARACTERS

2 Operating table
4 Object
6 Spine
8 Reference star
8a Reference star marking element
8b Reference star marking element
8c Reference star marking element
10 C-arm
12 X-ray source
14 X-ray detector or X-ray intensifier
16 Stereoscopic camera of the surgical operation navigation system
18 Reference marking
20 Coordinate transformation apparatus
22 Control device
24 Verification device
26 X-ray system instruction mechanism
28 Surgical operation navigation system instruction mechanism
30 X-ray system
32 Surgical operation navigation system

The invention claimed is:

1. A method of determining a reference object coordinate transformation between a surgical operation navigation system and an X-ray system having a pivotable C-arm designed to detect an interior of an object, the method which comprises:
    arranging marking elements of a reference object in a region that is detected by the surgical operation navigation system and in at least two pivoting positions of the C-arm by the X-ray system;
    detecting a position of the marking elements with the surgical operation navigation system;
    detecting the marking elements with the X-ray system from at least two projections;
    wherein each projection is taken from a different pivoting position of the C-arm;
    determining a position of the reference object from at least two two-dimensional projection images; and
    calculating the reference object coordinate transformation from the position of the marking elements detected by the surgical operation navigation system and the position of the marking elements determined by the X-ray system.

2. The method according to claim 1, wherein the arranging step comprising locating the marking elements in a region in which no three-dimensional image reconstruction is performed depicting the interior of the object.

3. The method according to claim 1, wherein, with at least one projection image, not all marking elements of the reference object are detected by the X-ray beam of the X-ray system.

4. A method of verifying a C-arm coordinate transformation between a surgical operation navigation system and an X-ray system with the C-arm, the method which comprises:
    detecting a position of a reference object with the surgical operation navigation system;
    pivoting the C-arm into at least two positions;
    detecting the position of the C-arm with the surgical operation navigation system after the pivoting;
    detecting data representing an interior of the object by way of X-radiation after the pivoting;
    calculating the C-arm coordinate transformation between the surgical operation navigation system and the X-ray system on a basis of the at least two positions of the C-arm detected by the surgical operation navigation system and the position of the reference object detected by the surgical operation navigation system; and
    verifying the C-arm coordinate transformation by comparing the C-arm coordinate transformation with the reference object coordinate transformation as determined by the method according to claim 1.

5. The method according to claim 1, which further comprises:
    generating tomographic images from the data representing the interior of the object; and
    displaying navigation information in the tomographic images.

6. A computer program product, comprising program code in non-transitory form to be loaded into a memory of a computer and, when processed by the computer, to perform the steps of the method according to claim 1.

7. A coordinate transformation apparatus for determining a reference object coordinate transformation between a surgical operation navigation system and an X-ray system, the apparatus comprising:
    an X-ray system instruction mechanism configured to output an instruction to an X-ray system having a pivotable C-arm and being designed to detect an interior of an object;
    a surgical operation navigation system instruction mechanism configured to output an instruction to a surgical operation navigation system; and
    a control device connected to said X-ray system instruction mechanism and to said surgical operation navigation system instruction mechanism, said control device being configured:
        by way of said surgical operation navigation system instruction mechanism, to instruct said surgical operation navigation system to detect the position of marking elements of a reference object;

by way of said X-ray system instruction mechanism, to instruct said X-ray system to detect the position of the marking elements of the reference object by taking X-rays from at least two projections;

wherein each projection is taken from a different pivoting position of the C-arm;

by way of said X-ray system instruction mechanism, to instruct said X-ray system to detect the position of the marking elements from at least two two-dimensional projection images; and to determine the reference object coordinate transformation from the position of the reference object detected by said surgical operation navigation system and the position of the reference object determined by said X-ray system.

8. The coordinate transformation apparatus according to claim 7, wherein said X-ray system is configured to determine the position of the marking elements from two-dimensional projection images, while the marking elements are located in a region in which no three-dimensional reconstruction of the interior of the object is performed.

9. The coordinate transformation apparatus according to claim 7, wherein, with at least one projection image, fewer than all reference elements of the reference object are detected by the X-ray beam of the X-ray system.

10. The coordinate transformation apparatus according to claim 7, which further comprises a verification device connected to communicate with said control device, and wherein said control device is configured:

by way of said surgical operation navigation system instruction mechanism, to instruct the surgical operation navigation system to detect the position of the marking elements of the reference object;

by way of said X-ray system instruction mechanism, to instruct said X-ray system to pivot the C-arm into at least two positions;

by way of said surgical operation navigation system instruction mechanism, to instruct said surgical operation navigation system to detect the position of the C-arm after the pivoting;

by way of said X-ray system instruction mechanism, to instruct said X-ray system to detect data representing the interior of the object by way of X-radiation after the pivoting;

to determine a C-arm coordinate transformation from the positions of the C-arm detected by said surgical operation navigation system and the position of the reference object detected by said surgical operation navigation system; and to instruct said verification device to compare the C-arm coordinate transformation with the reference object coordinate transformation.

11. The coordinate transformation apparatus according to claim 7, wherein said control device is configured:

by way of said X-ray system instruction mechanism, to instruct said X-ray system to generate tomographic images from the data representing the interior of the object; and by way of said surgical operation navigation system instruction mechanism, to instruct said surgical operation navigation system to display navigation information in the tomographic images.

12. A surgical operation system, comprising:
an X-ray system with a C-arm;
a surgical operation navigation system; and
a coordinate transformation apparatus according to claim 7.

13. A method of determining a reference object coordinate transformation between a surgical operation navigation system and an X-ray system having a pivotable C-arm designed to detect an interior of an object, the method which comprises:

arranging a reference star having three or more elements in a region that is detected by the surgical operation navigation system and in at least two pivoting positions of the C-arm by the X-ray system;

detecting a position of the marking elements with the surgical operation navigation system;

detecting the marking elements with the X-ray system from at least two projections;

wherein each projection is taken from a different pivoting position of the C-arm;

determining a position of the reference object from at least two two-dimensional projection images; and calculating the reference object coordinate transformation from the position of the marking elements detected by the surgical operation navigation system and the position of the marking elements determined by the X-ray system.

14. The method of claim 13, wherein the plurality of marking elements reflect light in the infrared range.

15. The method of claim 13, wherein the reference star is arranged on the patient.

* * * * *